(12) United States Patent
Okuno (10) Patent No.: US 11,382,953 B2
(45) Date of Patent: Jul. 12, 2022

(54) MICROVASCULAR BLOOD FLOW DECREASING AGENT AND USE THEREOF

(71) Applicant: Tetsuji Okuno, Tokyo (JP)

(72) Inventor: Tetsuji Okuno, Tokyo (JP)

(73) Assignee: Tetsuji Okuno, Tokyo (JP)

( * ) Notice: Subject to any disclaimer, the term of this patent is extended or adjusted under 35 U.S.C. 154(b) by 471 days.

(21) Appl. No.: 16/328,318

(22) PCT Filed: Feb. 24, 2017

(86) PCT No.: PCT/JP2017/007093
§ 371 (c)(1),
(2) Date: Feb. 26, 2019

(87) PCT Pub. No.: WO2018/037595
PCT Pub. Date: Mar. 1, 2018

(65) Prior Publication Data
US 2019/0192627 A1    Jun. 27, 2019

(30) Foreign Application Priority Data
Aug. 26, 2016 (JP) .............................. JP2016-165995

(51) Int. Cl.
| | | |
|---|---|---|
| C07K 16/28 | (2006.01) | |
| A61K 39/395 | (2006.01) | |
| A61P 29/00 | (2006.01) | |
| A61K 38/17 | (2006.01) | |
| A61P 9/00 | (2006.01) | |
| A61P 35/00 | (2006.01) | |
| A61K 45/06 | (2006.01) | |
| A61K 45/00 | (2006.01) | |
| C07K 14/705 | (2006.01) | |
| A61K 9/16 | (2006.01) | |
| A61K 31/138 | (2006.01) | |
| A61K 31/282 | (2006.01) | |
| A61K 31/337 | (2006.01) | |
| A61K 31/407 | (2006.01) | |
| A61K 31/513 | (2006.01) | |
| A61K 31/593 | (2006.01) | |
| A61K 31/69 | (2006.01) | |
| A61K 31/704 | (2006.01) | |
| A61K 31/7068 | (2006.01) | |
| A61K 35/36 | (2015.01) | |
| A61K 38/14 | (2006.01) | |
| A61K 38/36 | (2006.01) | |
| A61K 9/00 | (2006.01) | |

(52) U.S. Cl.
CPC ........ A61K 38/1774 (2013.01); A61K 9/0024 (2013.01); A61K 9/1688 (2013.01); A61K 31/138 (2013.01); A61K 31/282 (2013.01); A61K 31/337 (2013.01); A61K 31/407 (2013.01); A61K 31/513 (2013.01); A61K 31/593 (2013.01); A61K 31/69 (2013.01); A61K 31/704 (2013.01); A61K 31/7068 (2013.01); A61K 35/36 (2013.01); A61K 38/14 (2013.01); A61K 38/1793 (2013.01); A61K 38/366 (2013.01); A61K 39/395 (2013.01); A61K 39/3955 (2013.01); A61K 45/00 (2013.01); A61K 45/06 (2013.01); A61P 9/00 (2018.01); A61P 29/00 (2018.01); A61P 35/00 (2018.01); C07K 14/70503 (2013.01); C07K 14/70521 (2013.01); C07K 16/2803 (2013.01); C07K 16/2818 (2013.01); C07K 2317/76 (2013.01)

(58) Field of Classification Search
None
See application file for complete search history.

(56) References Cited

U.S. PATENT DOCUMENTS

| | | | | |
|---|---|---|---|---|
| 6,652,884 | B2 * | 11/2003 | Falciani ............... | A61K 9/5052 424/489 |
| 2003/0087961 | A1 * | 5/2003 | Ko ........................ | A61K 31/19 514/557 |
| 2007/0269406 | A1 * | 11/2007 | Ichim ................. | A61K 49/0447 424/85.2 |
| 2008/0020052 | A1 | 1/2008 | Li ................................ | 424/490 |
| 2008/0025979 | A1 | 1/2008 | Honjo et al. ............... | 424/136.1 |
| 2009/0202467 | A1 * | 8/2009 | Bock ...................... | A61K 31/77 424/78.38 |
| 2013/0078288 | A1 * | 3/2013 | Yu .......................... | A61K 47/12 424/400 |
| 2014/0155678 | A1 * | 6/2014 | Zeng .................. | C07K 16/2878 600/1 |
| 2015/0140021 | A1 * | 5/2015 | Kao ........................ | A61P 25/00 424/178.1 |

(Continued)

FOREIGN PATENT DOCUMENTS

| | | |
|---|---|---|
| JP | 2008-513381 A | 5/2008 |
| JP | 2015-74633 | 4/2015 |

(Continued)

OTHER PUBLICATIONS

Braun et al. (2021) Nature Reviews Clinical Oncology 18: 199-214.*
Bukamur et al. (2020) Southern Medical Journal, 113: 600-605.*
He et al. (2020) Cell Research 30: 660-669.*
Jiang et al. (2021) Genes & Diseases 8: 25-37.*
Khan et al. (2020) Front. Immunol. 11:167, 1-31.*
Krijgsman et al. (2020) Int. J. Mol. Sci. 21:4528, 1-10.*
Lee et al. (2021) Front. Pharmacol. 12:681320, 1-19.*
Lentz et al. (2021) Mol Cancer Ther. 20: 961-74.*

(Continued)

Primary Examiner — Ilia I Ouspenski
(74) Attorney, Agent, or Firm — Licata & Tyrrell P.C.

(57) ABSTRACT

The purpose of the present invention is to provide a novel medicinal agent that has an effect of decreasing a microvascular blood flow. Provided is a microvascular blood flow decreasing agent that contains an immune checkpoint inhibitor.

5 Claims, 4 Drawing Sheets

(56) References Cited

U.S. PATENT DOCUMENTS

| | | | | |
|---|---|---|---|---|
| 2015/0202291 | A1* | 7/2015 | Bosch | C07K 16/2818 424/156.1 |
| 2015/0335768 | A1* | 11/2015 | Quinn | A61K 49/101 424/1.69 |
| 2016/0257752 | A1* | 9/2016 | Kim | A61K 39/3955 |
| 2017/0182003 | A1* | 6/2017 | Bao | C07K 16/2827 |
| 2018/0117006 | A1* | 5/2018 | Poznansky | A61K 9/0019 |
| 2018/0207212 | A1* | 7/2018 | Conner | A61K 47/12 |
| 2019/0022203 | A1* | 1/2019 | Lichty | C12N 7/00 |
| 2019/0060255 | A1* | 2/2019 | Xu | A61K 39/395 |
| 2019/0083556 | A1* | 3/2019 | Lindstedt | C07K 16/2818 |
| 2020/0308294 | A1* | 10/2020 | Markovic | A61K 47/6855 |
| 2021/0283060 | A1* | 9/2021 | Okuno | A61K 45/06 |

FOREIGN PATENT DOCUMENTS

| | | |
|---|---|---|
| WO | 2004/072286 | 8/2004 |
| WO | 2016/130839 | 10/2016 |

OTHER PUBLICATIONS

Liu et al. (2021) Signal Transduction and Targeted Therapy 6:28, 1-11.*
Maker et al. (2005) Annals of Surgical Oncology, 12(12): 1005-1016.*
Marin-Acevedo et al. (2018) Journal of Hematology & Oncology 11:39, 1-20.*
Marin-Acevedo et al. (2021) J Hematol Oncol 14:45, 1-29.*
Nakajima et al. (2021) Cancer and Metastasis Reviews 40: 297-302.*
Sharma et al. (2015) Science 348(6230): 56-61.*
Tecentriq Labeling Package Insert (2016) FDA, 22 pages.*
Wei et al. (2018) Cancer Discov; 8(9): 1069-1086.*
Lipson et al. (2013) Cancer Immunol Res; 1(1); 54-63.*
Lou et al. (2016) Clin Cancer Res; 22(14); 3630-42.*
Ma et al. (2016) Journal of Hematology & Oncology, 9:47; 1-21.*
Mischinger et al. (2015) Curr Urol Rep 16:59; 1-6.*
Prendergast et al. (2014) Cancer Immunol Immunother; 63: 721-735.*
Remon et al. (2016) Curr Opin Oncol, 28: 122-129.*
Taube et al. (2012) Sci. Transl. Med., 4 (127); 1-10.*
Wang et al. (2015) Carcinogenesis, vol. 36, No. 10, 1085-1093.*
Extended Search Report in EP 17843086.4, Mar. 17, 2020, EP.
Hodi et al., "Bevacizumab plus Ipilimumab in Patients with Metastatic Melanoma" Cancer Immunology Research 2014 2(7):632-642.
Callahan M.K. & Wolchok J.D. "At the Bedside:CTLA-4 and PD-1-blocking antibodies in cancer therapy" J. Leukoc. Biol. 2013 94 41-53.
Hodi et al., "Biologic activity of cytotoxic T lymphocyte-associated antigen 4 blockade in previously vaccinated metastatic melanoma and ovarian carcinoma patients" Proc Natl Acad Sci U S A. Apr. 15, 2003;100(8):4712-7.
Momtaz et al., "Immunologic checkpoints in cancer therapy: focus on the programmed death-1 (PD-1) receptor pathway" Pharmacogenomics Pers Med. 2014 15(7):357-65.
Okuno, Tetsuji "Tokushu Gan Chiryo to Kekkannai Chiryo Gan no Kobetsuka Iryo to, Kekkannai Chiryo no Hatasu Yakuwari", Togo Iryo de Gan ni Katsu, 2014 75: 17-20.
Okuno, Tetsuji "Kekkan kara Gan o Naosu", [online], 18, Mar. 2016 (Mar. 18, 2016), [Retrieved on Apr. 12, 2017 (Apr. 12, 2017), Retrieved from the Internet: <URL: Http://www.clinica-et.com/docs/_2016_160313.pdf>.
Okuno, Tetsuji "CTL4, PD1, PDL1 Kotai o Mochiita Shinko Gan no Kekkannai Chiryo. Shuyo Kekkan Mitsudo no Genryou Koka to Chiryo Kankaku no Ensho Koka ni Tsuite", the 13th Annual Meeting of Japan Research Association for Immunotherapeutics, Feb. 2016, p. 59, P-21.
Paradis et al. et al., "The anti-tumor activity of anti-CTLA-3 is mediated through its induction of IFNγ" Cancer Immunol Immunotherapy, 2001, 50: 125-133.
English language translation of Okuno, Tetsuji "Tokushu Gan Chiryo to Kekkannai Chiryo Gan no Kobetsuka Iryo to, Kekkannai Chiryo no Hatasu Yakuwari", Togo Iryo de Gan ni Katsu, 2014 75: 17-20.
English language translation of Okuno, Tetsuji "Kekkan kara Gan o Naosu", [online], Mar. 18, 2016 (Mar. 18, 2016), [Retrieved on Apr. 12, 2017 (Apr. 12, 2017), Retrieved from the Internet: <URL: Http://www.clinica-et.com/docs/_2016_160313.pdf>.
English language translation of Okuno, Tetsuji "CTL4, PD1, PDL1 Kotai o Mochiita Shinko Gan no Kekkannai Chiryo. Shuyo Kekkan Mitsudo no Genryou Koka to Chiryo Kankaku no Ensho Koka ni Tsuite", the 13th Annual Meeting of Japan Research Association for Immunotherapeutics, Feb. 2016, p. 59, P-21.
Yoshikawa et al. "Intra-arterial chemotherapy for liver cancer" Clinical Gastroenterology 2006 21(7):255-261.
Tohnai, I. "Chemotherapy using intra-arterial infusion for oral cancer" Nagoya J Med 2006 68:101-108.
"New Drug Delivery System for Lung Cancer: About reservoir intra-arterial infusion therapy" 'Japanese Journal of Cancer and Chemotherapy 1995 22(1):77-82.
"Intra-arterial infusion therapy for head and neck malignancies" Japanese Journal of clinical Radiology 2006 51(11):1359-1363.

* cited by examiner

MICROVASCULAR BLOOD FLOW DECREASING AGENT AND USE THEREOF

This patent application is a U.S. National Stage Application of International Application No. PCT/JP2017/007093, filed Feb. 24, 2017, which claims the benefit of priority from Japanese Patent Application No. 2016-165995, filed Aug. 26, 2016, teachings of each of which are herein incorporated by reference in their entirety.

TECHNICAL FIELD

The present invention relates to a microvascular blood flow decreasing agent comprising an immune checkpoint inhibitor, a method for selectively decreasing blood flow of a microvasculature using an immune checkpoint inhibitor, and a method for treating tumor or inflammation using said method, etc.

BACKGROUND ART

Cancer cells and stromal cells in cancer tissue secrete angiogenic factors such as vascular endothelial growth factor (VEGF), and within the tissue form new vascular networks arborizing from existing vascular system. It is considered that these new vascular networks provide nutrients necessary for the growth of the cancer tissue and provide pathways for metastasis. Here, for the purpose of preventing nutrient supply from these tumor blood vessels to cancer tissue, attention has been payed to therapies for inhibiting tumor angiogenesis or for embolizing blood vessels and the like, and drugs for embolizing small vessels have been developed.

However, it is difficult to selectively embolize only tumor blood vessels because they form complicated vascular networks as mentioned above. Therefore, the method adopted in many cases is to inhibit nutritional transmission by embolizing the original vessel from which tumor vessels arborize. However, this method requires embolizing normal blood vessels and it is therefore concerned that there may be some influence on normal tissue.

In recent years, methods for delivering a drug to a specific part of a tissue have been attracting attention. This method, in which tumor site is specified by e.g., angiography, and a micro-catheter is inserted into the artery that is responsible for the nutrient supply to that tumor part, and a drug such as an anti-cancer agent is administrated through that micro-catheter, is called superselective intraarterial infusion, which is capable of selective delivery of drugs at high concentration to specific site with less side effects as compared to systemic chemotherapy and therefore is considered to have a high efficacy.

Thus, endovascular therapy using a medical equipment inserted into a blood vessel has been drawing attention as being capable of obtaining high efficacy with minimal invasion. However, therapeutic methods to various microvasculature including tumor vessels are in fact yet to sufficiently be in practical use in clinical application.

As the methods for treating cancer, surgical resection by operation, chemotherapy by anti-cancer agent administration, and radiotherapy by radiation are said to be the three major therapies. Recently, in addition to these, cancer immunotherapy has been paid attention as the fourth treatment method by which cancer is to be treated by means of the action of the immune system. Representative methods include those methods which use antibodies that target proteins specifically expressed by cancer cells and which use cytotoxic T-cells that specifically recognize cancer cells.

Conventional cancer immunotherapy was entirely directed to reinforce the immunological action against cancer. However, recently, the mechanism by which cancer escapes the action of immune system has been understood better. This immune escape by cancer cells involves a mechanism called immune checkpoint. Immune checkpoint is originally a system for suppressing excessive immune response and inhibiting development of diseases such as autoimmune diseases. There are proteins called immune checkpoint proteins on T-cell surface, which is bound to its ligand present on the surface of an autologous cell, thereby suppressing T-cell activation. Cancer cells also have the ligand of the immune checkpoint protein similarly on their surface, thereby escaping the attack by the cytotoxic T-cells (CTLs), etc.

Recently, attention has been paid to a method for treating cancer by means of autoimmune effect by inhibiting the action of this immune checkpoint protein or its ligand to decrease the immune evasion ability of cancer cells. As immune checkpoint inhibitory drugs, for example, nivolumab (anti-PD-1 antibody) and ipilimumab (anti-CTLA-4 antibody), etc. are commercially available.

PRIOR ART REFERENCES

Patent References

[Patent Reference 1]
JP A 2008-513381.

Non-Patent References

[Non-Patent Reference 1]
Hodi et al., Proc Natl Acad Sci USA. 2003 Apr. 15; 100(8):4712-7
[Non-Patent Reference 2]
Momtaz et al., Pharmgenomics Pers Med. 2014 Nov. 15; 7:357-65

SUMMARY OF THE INVENTION

Problem to be Solved by the Invention

The present invention is aimed to provide a novel drug that has an effect of decreasing blood flow of a microvasculature.

Means to Solve the Problem

The inventor carried on intensive investigation into endovascular therapy for cancer based on a finding that tumor vessel density decreases by injection of a nano-sized anti-cancer agent into the nutrient artery, and newly found that anti-CTLA-4 antibody ipilimumab, an immune checkpoint inhibitor which has been used in combination with the nano-sized anti-cancer agent, has a strong tumor vessel density-decreasing effect by itself. The inventor further carried on the investigation based on such new finding, and consequently found that other immune checkpoint inhibitors also have similar effect to complete the present invention.

Namely, the present invention relates to those listed below:
(1) Microvascular blood flow decreasing agent comprising an immune checkpoint inhibitor.
(2) The microvascular blood flow decreasing agent according to (1), wherein the microvasculature is a tumor vessel and/or a blood vessel at an inflammation site.
(3) The microvascular blood flow decreasing agent according to (1) and (2), wherein the immune checkpoint inhibitor is an inhibitor selected from the group consisting of anti-CTLA-4 antibody, anti-PD-1 antibody, and anti-PDL-1 antibody.
(4) The microvascular blood flow decreasing agent according to any one of (1) to (3), administered to the target vessel by a microcatheter.
(5) The microvascular blood flow decreasing agent according to any one of (1) to (4), wherein the immune checkpoint inhibitor is administered at a dosage of 1 to 50 mg per dose.
(6) The microvascular blood flow decreasing agent according to any one of (1) to (5), further used in combination with a nano-sized anti-cancer agent and/or anti-inflammatory agent.

Effects by the Invention

According to the present invention, a novel agent that is capable of decreasing blood flow through a microvasculature, particularly a tumor vessel or a blood vessel at an inflammation site is provided. In diseases having microvasculature, particularly in tumor site, vascular networks are complicated by over-developed microvasculature, causing congestion of blood stream due to an increased blood flow, leading to hypoxic state at disease site. However, the agent of the present invention can selectively decrease blood flow through microvasculature, can resolve blood stream congestion and improve hypoxic state around the microvasculature. By improving hypoxic state, the niche of cancer stem cells is deprived, which in turn suppresses the growth of cancer cells. As a consequence, the cancer can be treated. Because such mechanism exhibits its effect independent of the type of the organ which develops cancer, it is capable of establishing a method of treatment which is equally effective to any cancer.

According to the present invention, a novel application of an agent known as immune checkpoint inhibitor is provided. When it is used in an application of the present invention, the immune checkpoint inhibitor will exhibit its effect at a far smaller amount than its conventional effective dosage, greatly reducing the risk of side effects. Moreover, since the immune checkpoint inhibitors are relatively expensive drugs, the economic burden to the patient can greatly be reduced.

MODES FOR PRACTICING THE INVENTION

Hereinbelow, the present invention will be illustrated in details.

<1> Microvascular Blood Flow Decreasing Agent of the Present Invention

In the present invention, "microvasculature" means blood vessel(s) which constitutes a microvascular network that is developed de novo in specific disease site. Characteristics of microvasculature include its disorder and congestion relative to normal blood vessels, having a number of arteriovenous shunts and high permeability at vascular wall. Examples of microvasculature include, though not being limited thereto, such as, for example, a tumor vessel, a blood vessel at an inflammation site, a blood vessel around an ischemic site, and a blood vessel at a site having prolonged pain. In one embodiment of the present invention, microvasculature is preferably a tumor vessel or a blood vessel at an inflammation site, more preferably a tumor vessel.

In the present invention, a "tumor vessel" means a blood vessel which has typically been arborized de novo from existing blood vessel and which constitutes a disorderly and congested vascular network having many arteriovenous shunts observed in a tumor tissue. A tumor vessel is principally formed by angiogenic factors secreted by tumor cells and stromal cells in tumor tissue such as vascular endothelial growth factor (VEGF), has an instable structure with high permeability. This blood vessel not only supplies oxygen and nutrients to tumor cells, but also is involved in hematogenous metastasis.

In the present invention, a "blood vessel at an inflammation site" means a neovessel induced by inflammatory cytokines produced at an inflammation site, and typically includes a blood vessel that constitutes a vascular network developed de novo in rheumatic synovial membrane, for example.

In the present invention, a "blood vessel at a site having prolonged pain" means, in a pathologic condition diagnosed as osteoarthropathy, tendinosis or fasciitis, with chief complaint of chronic pain lasting for 3 months or longer, a blood vessel developed de novo in fascia, tendon or adipose tissue, etc. in a site having pain. Although these vessels would not indicate abnormal vascular density as clear as that in the vessels in tumor or inflammation site, there will be recognizable increase in vascular density accompanied with early venous visualization if observed well.

In the present invention, a "microvascular blood flow decreasing agent" means an agent that, upon being introduced into a microvasculature, has an effect of decreasing the amount of blood flow of said microvasculature. In one embodiment of the present invention, the decrease in the amount of blood flow can be caused by microvascular embolization. In another embodiment, the decrease in the amount of blood flow can be caused by microvascular destruction. Therefore, a microvascular blood flow decreasing agent includes, though not being limited thereto, such as, for example, a substance which embolizes a blood vessel, a substance which inhibits angiogenesis, and a substance which leaks from a blood vessel and decreases blood flow. A microvascular blood flow decreasing agent may be used in combination with another agent. For example, it may be used in combination with, e.g., an anti-cancer agent and anti-inflammatory agent, though not being limited thereto.

The present invention is based on a new finding that immune checkpoint inhibitors which usually are used in cancer immunotherapy, upon being introduced into a microvasculature, have an effect of decreasing blood flow of said microvasculature. Accordingly, the present invention in one aspect relates to a microvascular blood flow decreasing agent comprising an immune checkpoint inhibitor as an effective ingredient. The immune checkpoint inhibitor is an agent which suppresses T-cell activities and thereby suppresses excessive immune reaction, and inhibits the action of the immune checkpoint system directed to suppress development of autoimmune disease, etc. The immune checkpoint inhibitor has recently been used in cancer treatment as an agent which inhibits immune evasion by cancer cells. The microvascular blood flow decreasing agent of the present invention comprises an immune checkpoint inhibitor in an amount that, upon being administered into a microvasculature, is effective for decreasing blood flow of said microvasculature.

The immune checkpoint inhibitor that is used in the microvascular blood flow decreasing agent of the present invention may be any agent which has been known in the art as an immune checkpoint inhibitor, and includes, though not being limited thereto, such as, for example, an anti-CTLA-4, anti-PD-1, anti-PD-L1, anti-TIM-3, anti-LAG-3, anti-B7-H3, anti-B7-H4, anti-BTLA, anti-VISTA, and anti-TIGIT antibodies. In one embodiment of the present invention, an immune checkpoint inhibitor is preferably an anti-CTLA-4 antibody, an anti-PD-1 antibody and an anti-PD-L1 antibody, more preferably the anti-CTLA-4 antibody and anti-PD-1 antibody. Typical anti-CTLA-4 antibodies include ipilimumab, and typical anti-PD-1 antibodies include nivolumab and pembrolizumab, and typical anti-PD-L1 antibodies include atezolizumab and MSB0010718C (avelumab).

The mechanism by which an immune checkpoint inhibitor exhibits microvascular blood flow decreasing effect has not been clear in detail yet. However, the inventor has found that when an immune checkpoint inhibitor is prepared for administration into microvasculature, its particle diameter in the drug becomes approximately 10 to 15 nm. For example, in a case of tumor vessels, as mentioned above, it has been known that the structure of vascular wall is unstable with a high permeability, and drugs with small particle diameter, e.g., 40 nm or smaller, can easily permeate through it and arrive in tumor tissue. Therefore, without being bound by any theory, it can be considered that an immune checkpoint inhibitor can easily arrive in tumor tissue and can exhibit the blood flow decreasing effect.

The microvascular blood flow decreasing agent of the present invention reduces blood flow in microvascular network of a disease site, and thereby inhibits nutrient supply to the disease site and decrease abnormal neovessels, and thereby can treat the disease. Accordingly, diseases which have vascular networks of abnormal neovessels and which can be treated by the microvascular blood flow decreasing agent of the present invention typically include cancer and rheumatism.

In the present invention, "tumor" includes benign tumors and malignant tumors (cancers, malignant neoplasms). Cancer includes tumors of hematopoietic organs, epithelial malignant tumors (cancers, carcinomas) and non-epithelial malignant tumors (sarcomas). The agent of the present invention particularly exhibits its therapeutic effect in a cancer having tumor vessels, typically in a solid cancer.

As mentioned above, the immune checkpoint inhibitor has recently been used in cancer therapy. When it is used in a usual application, the cancer which can be treated is limited to cancer in which the corresponding immune checkpoint protein is involved in immune evasion. Nevertheless, when the immune checkpoint inhibitor is used as the microvascular blood flow decreasing agent of the present invention, the cancer which can be treated is not particularly limited. For instance, even when an anti-CTLA-4 antibody is used as the microvascular blood flow decreasing agent of the present invention, the cancer to be treated does not necessarily have to express CTLA-4.

Because the microvascular blood flow decreasing agent of the present invention exhibits its effect upon being introduced into a microvasculature, it typically is in an injectable form such as a liquid and an injection. Therefore, the microvascular blood flow decreasing agent of the present invention may comprise an immune checkpoint inhibitor and a pharmaceutically acceptable carrier. Pharmaceutically acceptable carriers include, though not being limited thereto, such as, for example, those which usually are used in the art as solvent or diluent for an injection, and typically include water and physiological saline.

In one embodiment of the present invention, the immune checkpoint inhibitor used in the microvascular blood flow decreasing agent is contained in the blood flow decreasing agent in a form which is easy to permeate microvascular vessel wall. The vessel wall of a microvasculature has an enhanced permeability as compared to a normal blood vessel. The permeability of the agent through vessel wall can further be increased by reducing its particle diameter. As mentioned above, the inventor has found that the particle size distribution of an immune checkpoint inhibitor is in a range between approximately 10 and 15 nm when it is prepared as a microvascular blood flow decreasing agent. Accordingly, the particle size distribution is preferably between 1 to 15 nm. In a preferred embodiment, the particle size distribution is between 10 and 15 nm. In another preferred embodiment, the particle size distribution is between 1 and 10 nm.

As a method for achieving a small particle size distribution, those which usually are used in the art such as, for example, shaking, dilution and stirring.

<2> Method of the Present Invention for Decreasing Microvascular Blood Flow

As mentioned above, the present invention originates with the new finding that an immune checkpoint inhibitor will exhibits an effect of decreasing blood flow upon being introduced into a microvasculature. Accordingly, the present invention in one aspect relates to a method for decreasing blood flow of a microvasculature by using an immune checkpoint inhibitor or a microvascular blood flow decreasing agent comprising an immune checkpoint inhibitor.

In therapy of progressive cancer with metastasis/recurrence, if chemotherapy which is standard therapy is ineffective, palliative care is often applied under the circumstance where the patient is capable of daily living, and it is often considered to be the case that the patient's wish for therapy cannot be met. The inventor has carried on therapies aimed to reducing tumor vessels by means of endovascular therapy for progressive cancers in which the standard therapy is ineffective. This is because, in a case where neither surgery, radiotherapy nor chemotherapy is effective, it is considered that an intervention rather into cancer microenvironment (cancer niche) than into cancer parenchyma would be important for maintaining QOL for longer period in favorable state. Nevertheless, it has become clear that the more intervention by endovascular therapy during treatment, the faster the reversal of proliferation (i.e., the reactivation of the cancer proliferation from the condition in which the therapy is effective for the cancer), making the control difficult. On the other hand, according to the method for decreasing microvascular blood flow using the immune checkpoint inhibitor of the present invention, intervals between therapies can remarkably prolonged as compared to conventional endovascular therapy, and thus it can be expected that the patient's QOL may be greatly improved.

The method of decreasing microvascular blood flow of the present invention comprises introducing an immune checkpoint inhibitor into a microvascular network in which a decrease in blood flow is desired. Administration may be systemic or local, as long as the immune checkpoint inhibitor can be introduced into the microvascular network.

In one preferred embodiment of the present invention, the immune checkpoint inhibitor is locally administrated into the microvasculature of the subject. Typical methods for local administration include intraarterial injection, and a method in which a catheter is introduced in the vicinity of the target vessel to directly administer the drug is particularly preferred. In the method of the present invention, because the target vessel is microvasculature, the catheter used is preferably a microcatheter in order to introduce the catheter in more vicinity of the target vessel. Methods for local administration into microvasculature using microcatheter is known in the art, and include, though not being limited thereto, such as, for example, superselective intraarterial infusion.

The inventor has found that the immune checkpoint inhibitor administered in the method of the present invention, particularly when being locally administrated, exhibits its effect in far smaller amount as compared to the case where it is used in its original application to suppress immune evasion by cancer cells. When it is used for decreasing microvascular blood flow according to the present invention, the dose of the immune checkpoint inhibitor to be administered will vary depending on the type of the immune checkpoint inhibitor to be administered, though a skilled person can calculate an appropriate amount. For example, it has been found that a decrease in microvascular blood flow and a change in tumor vessel density would occur by local administration of approximately 0.3 to 0.5 mg per supporting vessel in the case of ipilimumab, approximately 0.5 to 1 mg per supporting vessel in the case of nivolumab, and approximately 0.3 to 0.4 mg per supporting vessel in the case of pembrolizumab.

The lower limit of the dose to be administered is, for example, 0.1 mg or more, 0.2 mg or more, 0.3 mg or more, 0.4 mg or more, 0.5 mg or more, 1 mg or more, 2 mg or more, 3 mg or more, 4 mg or more or 5 mg or more, and the upper limit is, for example, 50 mg or lower, 45 mg or lower, 40 mg or lower, 35 mg or lower, 30 mg or lower, 25 mg or lower, 20 mg or lower, 15 mg or lower or 10 mg or lower. The range of the dosage to be administered may be determined as any combination of these upper and lower limits. Accordingly, the dosage to be administered is, for example, between 2 and 10 mg, between 3 and 30 mg, between 5 and 20 mg, between 5 and 45 mg, and the like. Moreover, the above dosage to be administered may be administered at once, or may be administered in multiple separate times.

The method of the present invention for decreasing microvascular blood flow can reduce blood flow of microvasculature in various diseases, and as a result can reduces microvascular density. Therefore, by using the method of the present invention for decreasing microvascular blood flow, diseases or symptoms in which microvascular hyperplasia is recognized can be treated. Accordingly, the present invention encompasses a method of treating a disease or symptom in which such microvascular hyperplasia is recognized. Diseases and symptoms that can be treated by the method of the present invention for decreasing microvascular blood flow include solid tumor, rheumatism, osteoarthropathy, tendinosis, fasciitis, spinal stenosis having chronic pain lasting for three months or longer as chief complaint, as well as various pain regarded as chronic pain syndrome. In the present invention the term "endovascular therapy", unless otherwise described, refers to a therapeutic method to treat a disease by administering to a microvasculature an agent that reduces the blood flow. Accordingly, as one embodiment of endovascular therapy, the method of the present invention for decreasing microvascular blood flow can suitably used.

<3> Method of the Present Invention for Treating Solid Tumor

The inventor has found that the microvascular blood flow decreasing agent of the present invention, upon being administered into a tumor vessel in particular, decreases the blood flow in said tumor vessel and thereby improves the hypoxic state and reduces tumor vessel density. Therefore, the microvascular blood flow decreasing agent of the present invention can be used in a method for treating solid tumor by improving microenvironment (niche) surrounding the solid tumor. Namely, the present invention in one embodiment relates to a method for treating solid tumor by decreasing blood flow of tumor vessels.

The method of the present invention for treating solid tumor can be performed by using a procedure called in general "endovascular therapy", and can be carried out in accordance with the method in <2> above for decreasing blood flow of the microvasculature. Accordingly, the method of the present invention for treating solid tumor comprises introducing an immune checkpoint inhibitor into the responsible vessel of the solid tumor and/or tumor vessels arborizing therefrom. As long as the immune checkpoint inhibitor can be introduced into the microvascular network, it may be administered systemically or locally.

As mentioned above, the method for treating solid tumor of the present invention decreases blood flow in tumor vessels which deliver nutrients to a solid tumor, decreases tumor vascular density, and thereby treats the solid tumor. Therefore, it can treat any tumor as long as it is a solid tumor which has tumor vessels. Therefore, tumors which can be treated include, though not being limited thereto, such as, for example, head and neck cancer, esophageal cancer, lung cancer, breast cancer, gastric cancer, liver cancer, bile duct cancer, pancreatic cancer, colorectal cancer, kidney cancer, bladder cancer, prostate cancer, testicular cancer, ovarian cancer, cervical cancer, endometrial cancer, malignant lymphoma and sarcoma.

Moreover, as mentioned above, the method for treating solid tumor of the present invention decreases blood flow in tumor vessels, thereby decreases tumor vascular density, and thereby exhibits therapeutic effect. Here, it is known that tumor vessels not only take a role in nutrient delivery to the tumor, but it also takes a role as a gateway for circulating tumor cells (CTCs). The method of the present invention enables blocking this gateway by decreasing tumor vascular density and eliminating tumor vessels, resulting in a decreased number of CTCs. This enables preventing tumor metastasis itself. Therefore, the solid tumor may be either primary or metastatic. According to the present invention, the tumor at metastatic site can be treated by treating the tumor at primary site. The tumor at the primary site can be treated the other way around by treating the tumor at the metastatic site.

WORKING EXAMPLES

The present invention will further be illustrated in detail with reference to following examples, which indicate specific examples of the present invention, but the present invention is not limited thereto.

Example 1. Outcome Assessment of Therapies with Regional Immune Checkpoint Inhibitor To 94 cases (48 males, 46 females, average age 62.1 years old), continuous treatment by local administration of immune checkpoint inhibitor was given, and short-term (1-month) reducing effect by the first therapy was examined for each disease stage. For 35 cases in which assessment of imaging 4 months after the first therapy was possible, long-term (4-month) reducing effect for each disease stage was further analyzed.

(1) Preparation of Regional Immune Checkpoint Inhibitor:

Either one of the immune checkpoint inhibitors (2 to 4 mg/body (2.2 mg/body on average) of anti-CTL4 antibody ipilimumab (YERVOY®, Bristol-Myers-Squibb), 4 to 45 mg/body (15.6 mg/body on average) of an anti-PD1 antibody nivolumab (Opdivo®, Bristol-Myers-Squibb), 2 to 20 mg/body (9.23 mg/body on average) of an anti-PD1 antibody pembrolizumab (Keytruda®, Merck Sharp & Dohme Limited) and 30 to 90 mg/body (60 mg/body on average) of an anti-PDL-1 antibody atezolizumab (Tecentriq®, Roche)), and anti-inflammatory agent (maxacalcitol, 10 to 20 μg/body and/or bortezomib, 0.35 to 0.7 mg/body, and/or etanercept, 25 mg/body, and/or thrombomodulin, 3200 to 6400 U/body) are dissolved in 100 to 150 ml of physiological saline and stirred using a stirrer, then introduced into responsible vessel.

(2) Results:

Short-term tumor-reducing effect in 1 month after the administration was assessed by MRI or CT imaging. Results are shown in the table below. In the table, CR indicates an elimination of tumor from the imaging, PR indicates >50% reduction of tumor diameter, MR indicates >30% reduction of tumor diameter, NC indicates <30% reduction of tumor diameter, and PD indicates an increase in tumor diameter.

TABLE 1

| Disease stage/Effect | CR | PR | MR | NC | PD | Total |
|---|---|---|---|---|---|---|
| I | 1 | 1 | 1 | 0 | 0 | 3 (3.2%) |
| II | 2 | 0 | 0 | 4 | 0 | 6 (6.4%) |
| III | 0 | 1 | 2 | 3 | 0 | 6 (6.4%) |
| IV | 0 | 6 | 8 | 39 | 26 | 79 (84.0%) |
| Total | 3 | 8 | 11 | 46 | 26 | 94 |
| | (R)/22 (23.4%) | | | 46 (48.9%) | 26 (27.6%) | 94 |

The assessment was carried out by classifying MR or higher as being effective. In subjects whose disease state is Stage I, II or III, short-term reducing effect was observed (8/15, 53.3%). However, in subjects at Stage IV, short-term reducing effect was not much expected (17.7% (14/79)), indicating there is a significant difference between disease stages.

Next, long-term tumor reducing effect for 4 month after administration was assessed by MRI or CT imaging. Results are shown in the table below.

TABLE 2

| Disease stage/Effect | CR | PR | MR | NC | PD | Total |
|---|---|---|---|---|---|---|
| I | 1 | 0 | 0 | 0 | 0 | 1 (2.9%) |
| II | 2 | 1 | 0 | 0 | 0 | 3 (8.6%) |
| III | 1 | 0 | 1 | 2 | 0 | 4 (11.4%) |
| IV | 1 | 5 | 1 | 10 | 10 | 27 (77.1%) |
| Total | 5 | 6 | 2 | 12 | 10 | 35 |
| | (R)/13 (37.1%) | | | 12 (34.3%) | 10 (28.6%) | 35 |

In the course of the treatment with the immune checkpoint inhibitor, further improvement was confirmed after 4 months (75% (6/8) in disease stages I, II and III, and 26% (7/27) even in disease stage IV), indicating that, although the short term tumor-reducing effect by the treatment with the immune checkpoint inhibitor is not as good as that by local administration of an anti-cancer agent, it exhibits a great effect in the long term.

(3) Assessment of the Reducing Effect for Different Diseases:

Tumor-reducing effect was assessed by calculating the average score in each disease group based on the scores designated as follows: CR=4, PR=3, MR=2, NC=1 and PD=0. Results are shown in the table below.

TABLE 3

| Disease group | Short-term effect | Number of Patients | Long-term effect | Number of Patients |
|---|---|---|---|---|
| Head and neck cancer | 1.87 | 6 | 3.67 | 3 |
| Breast cancer | 0.67 | 17 | 1.00 | 5 |
| Lung cancer | 1.79 | 14 | 2.33 | 6 |
| Gastrointestinal cancer | 0.78 | 18 | 1.00 | 5 |
| Liver/biliary/pancreatic cancer | 0.76 | 25 | 0.67 | 9 |
| Urogenital cancer | 1.55 | 11 | 1.60 | 5 |
| Sarcoma | 1.67 | 3 | 2.50 | 2 |
| Total | 1.11 | 94 | 1.54 | 35 |

In most disease groups, the results indicates higher effect in the long term than in the short term. In particular, a high effect was recognized not only in the short term but also in the long term in subjects having head and neck cancer, lung cancer, urogenital cancer (bladder cancer, ovarian cancer and endometrial cancer, in particular), or sarcoma. Moreover, in some cases of breast cancer, the reduction started after 8 to 11 months.

Example 2. Comparison with Conventional Endovascular Therapies (1) Groups Subjected to the Treatment:

The interval (days) between the two cancer endovascular therapies performed in the same case are compared between the subjects of 2462 cases. Group A (2137 cases) in which a nano-sized anti-cancer agent and anti-inflammatory agent are mainly used was compared with Group B (325 cases) in which either anti-CTL4, anti-PD1 or anti-PDL1 antibody are used with anti-inflammatory agent. Age, gender, disease stage (Stage 0 to IV) at the time of the therapy, ICD classification of the primary disease to be treated in Groups A and B2 are shown in the table below.

TABLE 4

| | Group A | Group B | 2010-2015 |
|---|---|---|---|
| Sample number | 2137 | 325 | 2462 |
| Male/female ratio (% male) | 40.24 | 37.54 | 39.89 |
| Average age at treatment | 58.8 | 58.7 | 58.8 |
| Median | 60 | 61 | 60 |
| STDEV | 12 | 12.1 | 12 |
| Disease stage | | | |
| 0 | 6 | 1 | 7 |
| 1 | 33 | 8 | 41 |
| 2 | 63 | 13 | 76 |
| 3 | 156 | 33 | 189 |
| 4* $P < 0.05$ | 1879 (87.9%) | 270 (83.1%) | 2149 (87.3%) |

(2) Method of Treatment:

Before the therapy, the disease site was imaged by MRI or CT, and the target vessel was searched from that image to identify the tumor vessel in as many lesions as possible for subsequent endovascular therapy.

In Group A, mainly nano-sized anti-cancer nanoagents (gemcitabine 200 mg/body, glycyrrhizinate 80 mg/body, oxaliplatin 50 mg/body, mitomycin 4 mg/body, Abraxane® 25 mg/body) are mixed to make particle ratio distribution of between 60 and 120 nm, and anti-inflammatory agents (maxacalcitol, 10 to 20 μg/body, bortezomib, 0.35 to 0.7 mg/body, etanercept, 25 mg/body, thrombomodulin, 3200 to 6400 U/body) are infused into the responsible vessel. The therapy was aimed to decrease the tumor vessel density. For the purpose of generating a nano-sized drug with less aggregation, optionally an uraninite ore was used to irradiate radiation of 150 μSv/h for 30 minutes to the drug and reduces the particle diameter distribution to the range between 3 and 5 nm, then stirred with a stirrer until being administered by infusion.

In Group B, an immune checkpoint inhibitor (either of anti-CTL4 antibody ipilimumab (YERVOY®, Bristol-Myers-Squibb) 2 to 10 mg/body, anti-PD1 antibody nivolumab (Opdivo®, Bristol-Myers-Squibb) 5 to 45 mg/body, anti-PD1 antibody pembrolizumab (Keytruda®, Merck Sharp & Dohme Limited) 5 to 20 mg/body, or an anti-PDL-1 antibody atezolizumab (Tecentriq®, Roche) 30 to 90 mg/body, and an anti-inflammatory agent (maxacalcitol 10 to 20 μg/body, bortezomib 0.35 to 0.7 mg/body, etanercept 25 mg/body, thrombomodulin 3200 to 6400 U/body) are dissolved in 100 to 150 ml of physiological saline and stirred with a stirrer until being infused into responsible tumor vessel. The therapy was aimed to decrease the tumor vessel density. These drugs were prepared in a clean bench inside the endovascular therapy room.

(3) Results:

The results are shown in the table below. As seen from the table below, the interval between therapies was clearly increased in Group B as compared to Group A, meaning that the immune checkpoint inhibitor exhibits an effect as blood flow decreasing agent for endovascular therapy, and that its effect last longer than conventionally used blood flow decreasing agents in endovascular therapy.

TABLE 5

| Therapy interval analysis/ | Group A | Group B |
|---|---|---|
| Mean (days) | 46 | 56.8 |
| Median (days) | 35 | 45 |
| 1st quartile value | 28 | 28 |
| 3rd quartile value | 52 | 64 |
| SDM | 34.8 | 42.3 |
| Sample number | 2137 | 325 |
| SEM | 0.8 | 2.3 |
| Confidence interval | 44.5-47.5 | 52.2-61.4 |

Figure 1:
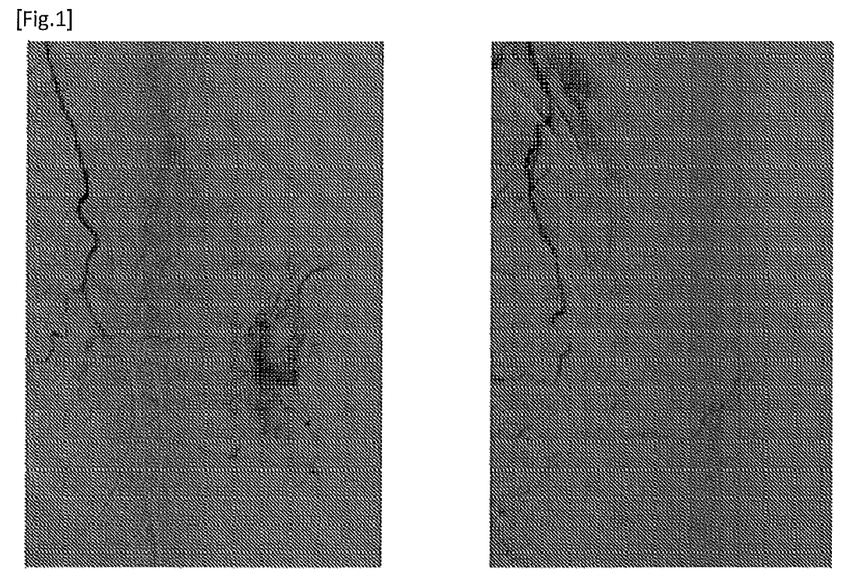
FIG. 1 shows photographs indicating the appearance of tumor vessels at disease site before and after endovascular therapy using a an immune checkpoint inhibitor to Patient A having breast cancer. The left is the picture before administration, the right is after administration. It can be seen that tumor vessels have been eliminated in the right picture.

Example 3. Cases (1) Patient a with Breast Cancer:

To Patient A who had suffered from breast cancer, an endovascular therapy was carried out using nivolumab 10 mg, pertuzumab 60 mg, bortezomib 0.7 mg, thrombomodulin 3200 U and maxacalcitol 10 μg. This patient was marked as CR by such treatment. Appearance of the tumor vessel in the lesion site is shown in FIG. 1.

Figure 2:
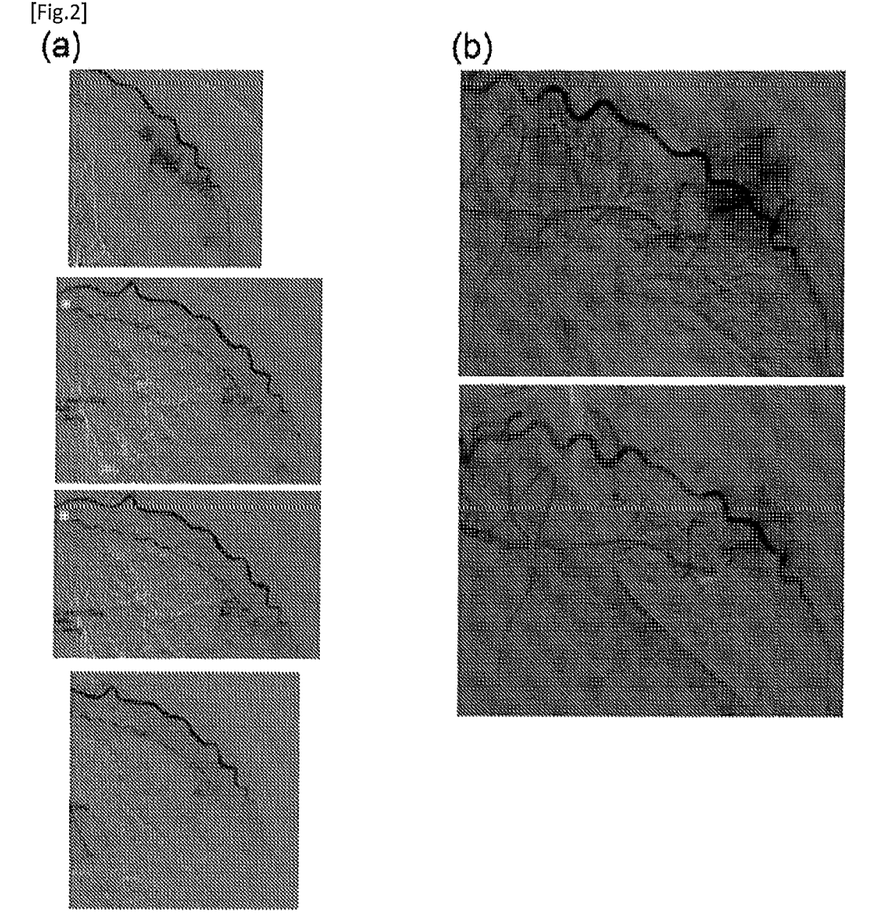
FIG. 2 shows photographs indicating the appearance of tumor vessels at disease site before and after endovascular therapy using a an immune checkpoint inhibitor to Patient B having malignant fibrous histiocytoma in right femur. (a) From top, pictures before endovascular therapy, after the first endovascular therapy, after the second endovascular therapy, and after the third endovascular therapy. (b) Pictures before endovascular therapy (top) and after the third endovascular therapy (bottom) at a different site.

(2) Patient B with Right Femoral Malignant Fibrous Histiocytoma (with Metastasis to Lung):

To Patient B who had suffered from malignant fibrous histiocytoma in right femur, an endovascular therapy was carried out using 20 mg of nivolumab. This patient was marked as CR after 3 treatments using 20 mg of nivolumab per each administration. Appearance of the tumor vessel in the lesion site is shown in FIG. 2.

Figure 3:
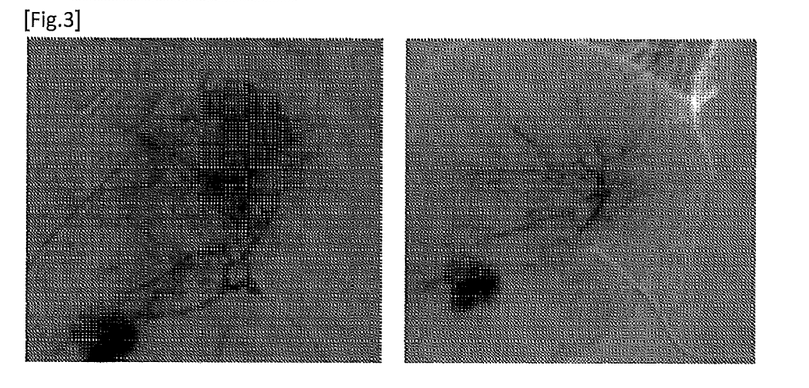
FIG. 3 shows photographs indicating the appearance of tumor vessels at disease site before and after endovascular therapy using a an immune checkpoint inhibitor to Patient C having liver cancer. The left is the picture before endovascular therapy, the right is after endovascular therapy.

(3) Patient C with Liver Cancer (Hepatitis C), T2N0M0 (Disease Stage II):

To Patience C who had suffered from hepatitis C and had developed liver cancer, an endovascular therapy was carried out using nivolumab 10 mg, bortezomib 0.7 mg, etanercept 25 mg, maxacalcitol 10 μg and imipenem/cilastatin sodium 500 mg/body for each administration. This patient was marked as CR after two treatments. Appearance of the tumor vessel in the lesion site is shown in FIG. 3.

Figure 4:
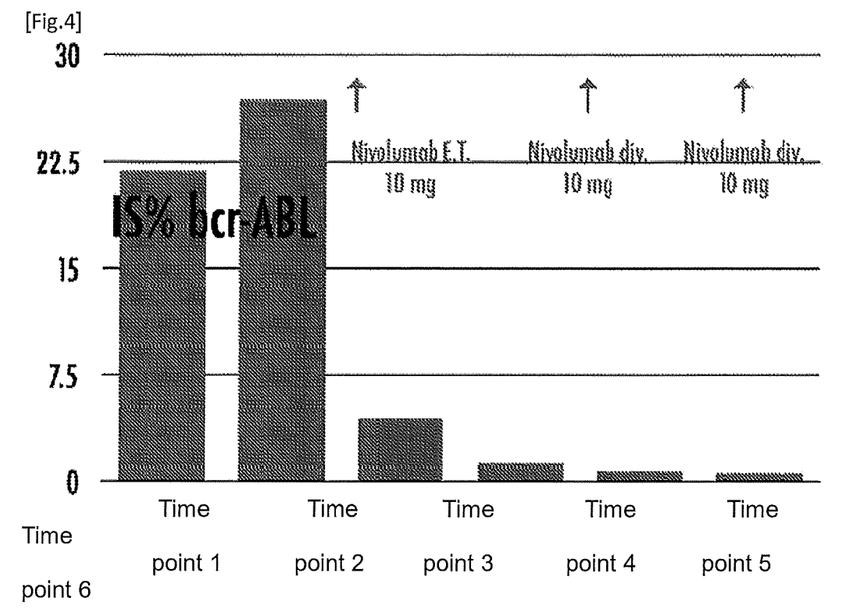
FIG. 4 shows a graph indicating the transition of % IS of bcr-ABL, a marker for chronic myeloid leukemia, over the time points 1 to 6 which cover the range before and after endovascular therapy using an immune checkpoint inhibitor against bladder cancer in Patient D having bladder cancer (chronic myeloid leukemia). It can be seen that bcr-ABL dramatically decreased between the time point 2, when the endovascular therapy for bladder cancer was performed, and the time point 3.

(4) Patient D with Bladder Cancer (Chronic Myeloid Leukemia), T2N0M0 (Disease Stage II):

In Patient D who had suffered chronic myeloid leukemia, a bladder cancer with muscle invation was found, suggesting a metastatic cancer. This patient was subjected to an endovascular therapy using nivolumab 10 mg, bortezomib 0.7 mg, etanercept 25 mg, maxacalcitol 10 μg, and thrombomodulin 3200 U, and was marked as CR by such treatment. After the endovascular therapy, the % IS of BCR-ABL mRNA, a marker for chronic myeloid leukemia, was also decreased, and it was determined that chronic myeloid leukemia was ameliorated, too. FIG. 4 is a graph showing the transition of % IS of BCR-ABL mRNA before and after the endovascular therapy for the bladder cancer in this patient.

DISCUSSION

It was shown that each of the immune checkpoint inhibitors causes a clear change in tumor hemodynamics by single-agent administration 2 to 3 minutes after the infusion from the tumor vessel. Moreover, an immediate relief from cancerous pain by administration is also confirmed. Adding to these, their original effect of inhibiting immune checkpoint can also be expected, providing a prospective of relatively longer lasting effect by administration of single agent. It is considered that the effect of extending the interval between therapies as indicated was exhibited as a consequence.

Example 4. Endovascular Therapy to Blood Vessels at a Site Having Prolonged Pain To 14 subject cases indicated in the table below who had blood vessels at a site having prolonged pain, endovascular therapy was carried out as follows, using pembrolizumab.

In all cases, fat suppression T2-weighted MRI image was obtained before treatment to select target vessels. 3Fr intraarterial-indwelling sheath (Medikit Co., Ltd.) was inserted from femoral artery by Seldinger method, allowed to reach the target vessel using 3Fr angiography catheter (Medikit Co., Ltd.), Radifocus 0.032" external diameter guide wire (TERUMO Corp.), and microcatheter ASAHI Tellus C3, ASAHI Meister 0.016" micro guide wire (ASAHI INTECC Co., Ltd.) as appropriate, then abnormal vascular networks are identified by contrast imaging.

Subsequently, as shown in the table, pembrolizumab 1 to 4 mg/body (mean=1.86 mg/body, median=2 mg/body) was mixed with the combined drugs in 100 ml of physiological saline, stirred with a stirrer while being infused into the target vessel in an amount such that a sufficient decrease in abnormal vessel density was confirmed.

The level of post-treatment improvement in symptoms was assessed after 3 weeks or longer. A stepwise assessment was done as follows: an exacerbation in symptom=0, no change=1, an improvement in symptom and easiness in dairy living=2, almost satisfactory improvement=3. Rating of 2 or more, i.e., an improvement in symptom was observed in 11 cases out of 14 cases (see, the table below). No side effect which was considered to be caused by the regional immune checkpoint inhibition therapy was observed in all cases, including minor side effects such as transient fever.

TABLE 6

| Case | Gender | Age | Disease identity | Disease duration (year) | P Dosage (mg/body) | Arterial infusion combined drug | Side effect | Effect |
| --- | --- | --- | --- | --- | --- | --- | --- | --- |
| Case 1 | F | 56 | Left gonarthritis | 9 | 1 | imp/cs 500, bv 50, bort 0.35, maxa 10, | 0 | 1 |
| Case 2 | F | 62 | Elbow joint RA | 5 | 4 | eta 25, bort 0.35, imp/cs 500 | 0 | 3 |
| Case 3 | F | 53 | Hip osteoarthritis | 5 | 3 | eta 25, bort 0.35, maxa 10, imp/cs 501 | 0 | 3 |
| Case 4 | F | 67 | Left shoulder pain | — | 3 | bort 0.35 | 0 | 3 |
| Case 5 | M | 79 | Lumbar spinal stenosis | 5 | 2 | bort 0.36 | 0 | 2 |
| Case 6 | F | 73 | Right foot Lisfranc joint injury | 20 | 1 | bv 50, bort 0.35, eta 25, maxa 10 | 0 | 3 |
| Case 7 | F | 80 | Low back pain after spinal compression fracture | 1.5 | 1 | bort 0.35, eta 25, maxa 10, reco 3200 | 0 | 2 |
| Case 8 | F | 73 | Right knee RA | 3.8 | 2 | bort 0.35, eta 25, reco 3200 | 0 | 2 |
| Case 9 | F | 81 | Bilateral knee joint replacement postoperation | 1.5 | 2 | eta 25, imp/cs 500 | 0 | 1 |
| Case 10 | F | 56 | Piriformis syndrome | 6 | 1 | bort 0.35, eta 25, reco 3200 | 0 | 2 |
| Case 11 | F | 43 | Left Achilles peritendinitis | 14 | 1 | | 0 | 3 |
| Case 12 | F | 59 | Bilateral gonarthrosis | — | 2 | | 0 | 2 |
| Case 13 | M | 77 | Left gonarthrosis, foot arthritis | 20 | 2 | | 0 | 1 |
| Case 14 | M | 61 | Right foot joint MFP syndrome | 3 | 1 | | 0 | 2 |

In the table, "imp/cs" denotes imipenem/cilastatin sodium, "bort" denotes bortezomib, "bv" denotes Avastin® (bevacizumab), "maxa" denotes maxacalcitol, "eta" denotes etanercept, and "reco" denotes thrombomodulin.

Figure 5:
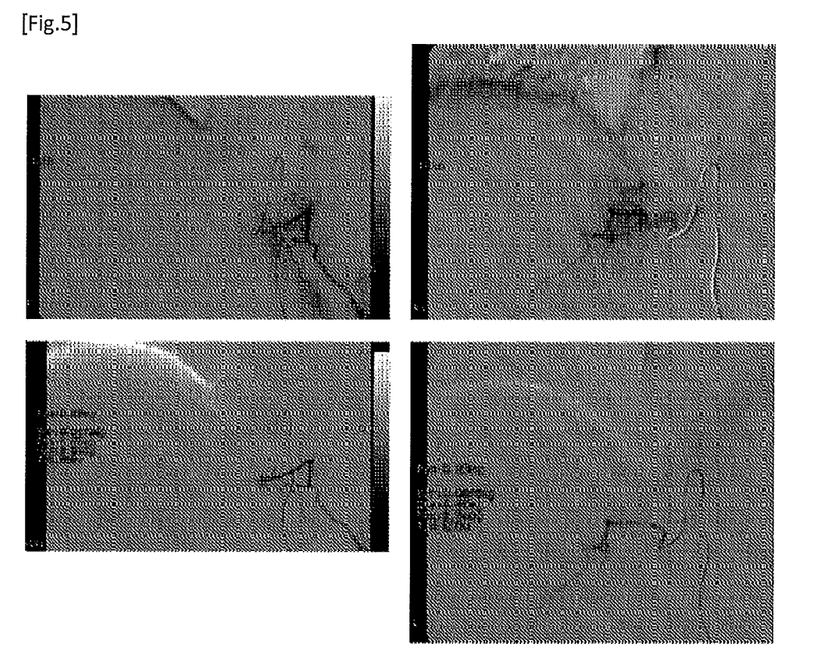
FIG. 5 shows photographs indicating the appearance of microvasculature at the disease site before and after endovascular therapy using an immune checkpoint inhibitor to a subject (Case 7) who complains of back pain after cementoplasty for vertebral compression fracture. The left and right pictures are contrastradiographs of the left and right 12th thoracic intercostal arteries, respectively, and the upper row is before the endovascular therapy, and the lower row is 2 minutes after drug administration by the endovascular therapy.
Figure 6:
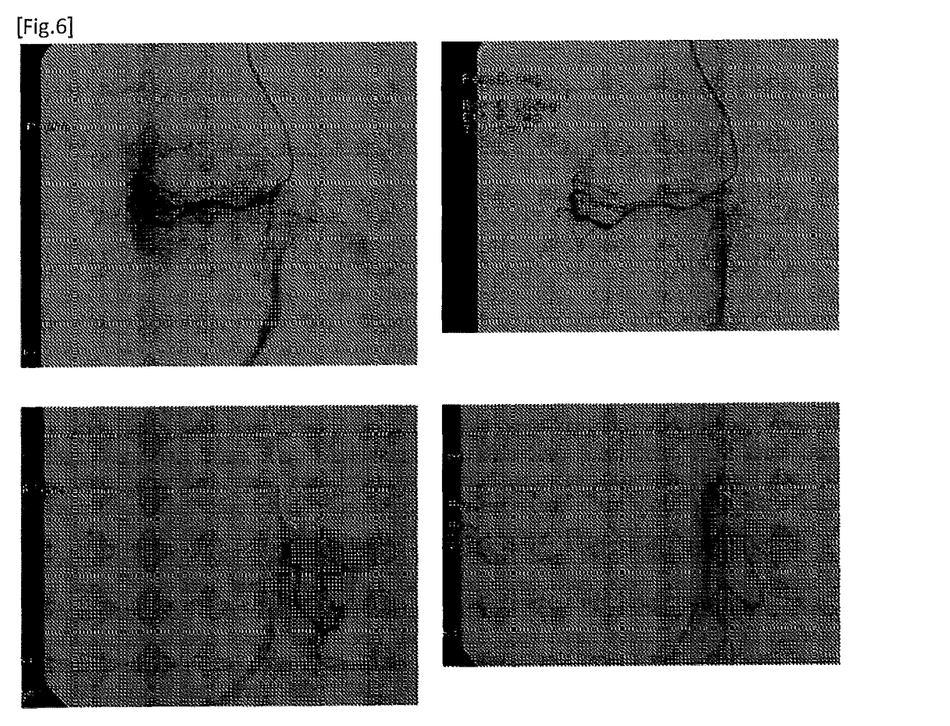
FIG. 6 shows photographs indicating the appearance of microvasculature at the disease site before and after endovascular therapy using an immune checkpoint inhibitor to a subject (Case 8) who has rheumatoid arthritis in right knee. The upper row shows contrastradiographs of lateral inferior genicular artery, the lower row shows inferior middle genicular artery, each left picture is before therapy, right picture is 2 minutes after drug administration. In each picture, a decrease in vessel density and elimination of visualization of veins by early arteriovenous shunt can be seen.

For Cases 7 and 8, the appearance of the microvasculature in the lesion site is shown in FIGS. 5 and 6, respectively. In Case 7, drugs are administered to four arteries, which are the lateral (left and right) 12th thoracic vertebral intercostal arteries and left and right 1st lumbar arteries, in amount described in the table above as total dosage. In Case 8, drugs are administered to lateral inferior genicular artery, middle superior genicular artery, descending genicular artery (superior medial), lateral/medial superior genicular artery, anterior tibial recurrent artery, and 8 knee joint nutrient arteries in amount described in the table above as total dosage. In both figures, the pictures after the therapy were taken 2 minutes after the drug administration. In both cases, significant decrease in abnormal microvascular density was confirmed only after 2 minutes.

DISCUSSION

A selective arterial infusion of the immune checkpoint inhibitor (pembrolizumab) solution diluted at 1 to 2% in physiological saline, which is in a small amount as little as 1 to 2 mg/body, to the site of pain enables the cancellation of chronic pain, indicating that such treatment will be a safe and economic therapy without any side effects.

Since the immune checkpoint inhibitor therapy clearly improves continuation of angiogenesis at the site of prolonged pain, it is suggested that the angiogenetic state itself that is associated with the prolonged pain has become intractable via immunotolerance, suggesting an involvement of CD8+ T lymphocytes at local environment. A regional immune checkpoint inhibition therapy (RCBT) as a fundamental pain therapy is expected.

INDUSTRIAL APPLICABILITY

It has been indicated that, according to the present invention, the immune checkpoint inhibitor administered to tumor vessels causes a clear change in tumor hemodynamics and thereby results in a remarkably higher therapeutic effect than that expected by conventional administration method. Moreover it has been found that the use of the immune checkpoint inhibitor as an agent for decreasing blood flow of microvasculature including tumor vessels enables a treatment with longer interval as compared to conventional intravenous therapy, which can make a substantial contribution to the improvement in QOL for a patient with advanced cancer. Furthermore, in the present invention the agent is principally locally administered and thus can exhibit its effect in smaller amount as compared to that in conventional administration method, and therefore can decrease economic burden when an expensive immune checkpoint inhibitor is used.

The invention claimed is:

1. A method for treating inflammation in a subject in need thereof, said method comprising:
   administering a microvascular blood flow decreasing agent comprising an immune checkpoint inhibitor by injection into an artery responsible for nutrient supply to a site of inflammation of the subject to decrease blood flow through a microvasculature that is blood vessel(s) which constitutes a microvascular network that is developed de novo in the inflammation site of the subject,
   wherein the immune checkpoint inhibitor is an antibody selected from the group consisting of anti-CTLA-4, anti-PD-1, anti-PD-L1, anti-TIM-3, anti-LAG-3, anti-B7-H3, anti-B7-H4, anti-BTLA, anti-VISTA and anti-TIGIT.

2. The method of claim 1, wherein the microvasculature is a blood vessel at an inflammation site.

3. The method of claim 1, wherein the microvascular blood flow decreasing agent is administered by a microcatheter.

4. The method of claim 1, wherein the immune checkpoint inhibitor is administered at a dosage of 1 to 50 mg per dose.

5. The method of claim 1, wherein the microvascular blood flow decreasing agent is administered in combination with a nano-sized anti-inflammatory agent.

* * * * *